United States Patent

Mathey et al.

[11] Patent Number: 6,166,257
[45] Date of Patent: Dec. 26, 2000

[54] ASYMMETRIC HYDROGENATION METHOD OF A KETONIC COMPOUND AND DERIVATIVE

[75] Inventors: Francois Mathey, Paris; Frederic Robin, Montrouge; Francois Mercier, Versailles; Michel Spagnol, Lyons, all of France

[73] Assignee: Rhodia Chimie, Courbevoie Cedex, France

[21] Appl. No.: 09/202,665

[22] PCT Filed: Jun. 27, 1997

[86] PCT No.: PCT/FR97/01154

§ 371 Date: Mar. 24, 1999

§ 102(e) Date: Mar. 24, 1999

[87] PCT Pub. No.: WO98/00375

PCT Pub. Date: Jan. 8, 1998

[30] Foreign Application Priority Data

Jun. 28, 1996 [FR] France ................................. 96 08060

[51] Int. Cl.$^7$ .................... C07C 211/43; C07C 49/04; C07C 49/12
[52] U.S. Cl. .................... 564/305; 564/150; 564/318; 546/134; 568/814; 568/880; 568/308; 568/361
[58] Field of Search ............... 556/21, 20; 568/705, 568/361, 715, 808, 811, 814, 840, 852, 878, 880, 844, 308, 12; 564/463, 305, 318, 464, 80, 89, 150; 562/564, 579, 465; 546/134

[56] References Cited

U.S. PATENT DOCUMENTS

| | | | |
|---|---|---|---|
| 3,636,091 | 1/1972 | Mason | 260/514 |
| 5,426,223 | 6/1995 | Burk | 564/150 |
| 5,516,944 | 5/1996 | Broger | 568/13 |
| 5,783,738 | 7/1998 | Mathey | 568/12 |
| 5,801,263 | 9/1998 | Seitz | 558/155 |
| 5,874,600 | 2/1999 | Rautenstrauch | 536/136 |

FOREIGN PATENT DOCUMENTS

| | | |
|---|---|---|
| 0 302 021 | 2/1989 | European Pat. Off. |
| 0 437 690 | 7/1991 | European Pat. Off. |
| 2 693 190 | 1/1994 | France |
| 95 21151 | 8/1995 | WIPO |
| 96 20202 | 7/1996 | WIPO |

OTHER PUBLICATIONS

A. Bréque et al, "The use of 1-phosphanorbornadienes with chiral phosphorus at the bridgehead in catalytic asymmetric hydrogenation of dehydroaminoacids", New Journal of Chemistry, vol. 13, No. 4/5, 1989, pp. 369–374, XP000618266, see p. 370.

*Primary Examiner*—Jean F Vollano
*Attorney, Agent, or Firm*—Burns, Doane, Swecker & Mathis, L.L.P.

[57] ABSTRACT

The present invention relates to a process for the asymmetric hydrogenation of a ketonic compound and derivative.

The invention relates to the use of optically active metal complexes as catalysts for the asymmetric hydrogenation of a ketonic compound and derivative.

The process for the asymmetric hydrogenation of a ketonic compound and derivative is characterized in that the asymmetric hydrogenation of said compound is carried out in the presence of an effective amount of a metal complex comprising as ligand an optically active diphosphine corresponding to one of the following formulae:

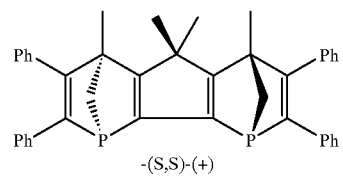

(Ia)

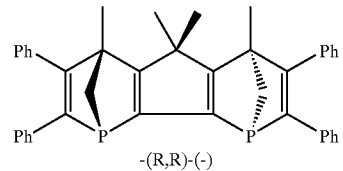

(Ib)

29 Claims, No Drawings

ASYMMETRIC HYDROGENATION METHOD OF A KETONIC COMPOUND AND DERIVATIVE

This application is the national stage of PCT/F97/01154, filed Jun. 27, 1997, now WO98/00375.

The present invention relates to a process for the asymmetric hydrogenation of a ketonic compound and derivative.

The invention relates to the use of optically active metal complexes as catalysts for the asymmetric hydrogenation of a ketonic compound and derivative.

French patent application no. 94/15757 and PCT/FR95/01716 describe novel optically active diphosphines of bis[1-phospha-2,3-diphenyl-4,5-dimethylnorbornadiene] of the following formulae:

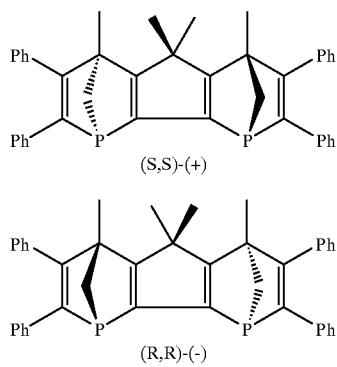

The novel phosphines are obtained by a process for resolving the racemic mixture of bis[1-phospha-2,3-diphenyl-4,5-dimethylnorbornadiene], which consists in reacting it with a palladium or platinum complex as a chiral auxiliary, in an organic solvent, to form diastereoisomeric complexes, and then resolving said optically pure complexes.

The mixture of the two starting diastereoisomers (on the one hand a meso complex and on the other hand a racemic complex) can be obtained according to the teaching described by F. Mathey et al. in Bull. Soc. Chim. Fr. 129, pp. 1–8 (1992).

In the process of the invention described in FR no. 94/15757, the racemic mixture of bis[1-phospha-2,3-diphenyl-4,5-dimethylnorbornadiene] is resolved by being reacted with a palladium or platinum complex as a chiral auxiliary.

It is possible to use a palladium complex. This type of chiral auxiliary is widely described in the literature, especially by Sei Otsuka et al. in Journal of the American Chemical Society 93, p. 4301 (1971).

It is also possible to use a platinum complex and reference may be made more particularly to the work of A.C. Cope [Journal of the American Chemical Society 90, p. 909 (1968)].

More particularly, the chiral complex used has general formula (VII):

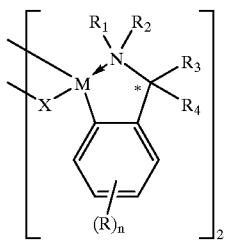

in which:
M is palladium and/or platinum;
$R_1$, $R_2$, $R_3$ and $R_4$ are a hydrogen atom, an alkyl radical having from 1 to 10 carbon atoms or a cycloalkyl radical having from 3 to 10 carbon atoms;
$R_3$ and $R_4$ are different and at least one of the two is a hydrogen atom;
R is as defined for $R_1$, $R_2$, $R_3$ and $R_4$;
X is a halogen atom; and
n is a number from 0 to 4; and
if n is greater than 1, two radicals R and the 2 adjacent atoms of the benzene ring can together form a ring having from 5 to 7 carbon atoms.

More preferably, the complex used has the above-mentioned formula in which $R_1$, $R_2$, $R_3$ and $R_4$ are a hydrogen atom or a methyl radical, X is a chlorine atom and n is equal to 0.

If n is equal to 2, two radicals R form a benzene ring.

The following may be mentioned as a more specific example of a palladium complex suitable for the present invention, arbitrarily obtained from (R)-(+)- or (S)-(−)-N,N-dimethylphenylethylamine:

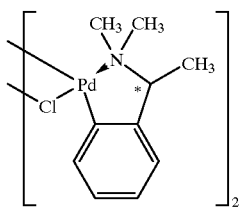

The amount of complex of the above-mentioned metals, expressed in terms of metal, is generally 0.5 to 1 metal atom per phosphorus atom.

An organic solvent which solubilizes all the reactants is used. It must be inert towards the diphosphine.

The following may be mentioned as non-limiting examples of solvents which are suitable in the process of the invention:
aliphatic hydrocarbons and more particularly paraffins such as especially pentane, hexane, heptane, octane, isooctane, nonane, decane, undecane, tetradecane, petroleum ether and cyclohexane; and aromatic hydrocarbons such as especially benzene, toluene, xylenes, ethylbenzene, diethylbenzenes, trimethylbenzenes, cumene, pseudocumene and petroleum cuts consisting of a mixture of alkylbenzenes, especially cuts of the Solvesso® type; and
aliphatic or aromatic halogenated hydrocarbons, e.g. perchlorinated hydrocarbons such as especially trichloromethane and tetrachloroethylene; and partially chlorinated hydrocarbons such as dichloromethane, dichloroethane, tetrachloroethane, trichloroethylene, 1-chlorobutane, 1,2-dichlorobutane, monochlorobenzene, 1,2-dichlorobenzene, 1,3-dichlorobenzene, 1,4-dichlorobenzene or mixtures of different chlorobenzenes.

Among all these solvents, benzene and toluene are preferred.

The concentration of the diphosphine in the reaction solvent is preferably between 0.05 and 1 mol/liter and particularly preferably between 0.05 and 0.2 mol/liter.

The separation is advantageously performed at room temperature, generally between 15° C. and 25° C.

It preferably takes place under a controlled atmosphere of inert gases. It is possible to establish an atmosphere of rare gases, preferably argon, but it is more economic to use nitrogen.

This gives a mixture of complexes of palladium or platinum and diphosphine corresponding to each enantiomer.

More particularly, said complexes have the following formulae:

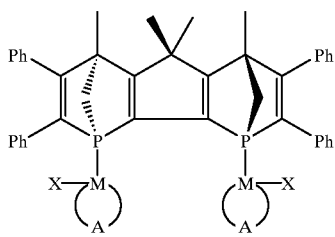

(VIII a)

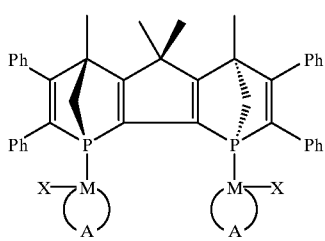

(VIII b)

in which M is palladium or platinum, X is a halogen atom, preferably chlorine, and A symbolizes the rest of a chiral metal complex of formula (VII) or, preferably, (VII').

The two pure enantiomers are recovered in a subsequent step.

The solvent is concentrated by evaporation and the separation is then carried out in known manner [A. Bertheillier—Dunod Paris (1972)] by liquid chromatography on a column, preferably with a silica support.

The column is eluted with a mixture of appropriate solvents, preferably a toluene/ethyl acetate mixture preferably comprising 80% by volume of toluene and 20% by volume of ethyl acetate.

The two pure enantiomers isolated are recovered in the form of two diastereoisomeric complexes having the following characteristics:

$^{31}$P NMR: $\delta(CH_2Cl_2)$=55.9 ppm
$^{31}$P NMR: $\delta(CH_2Cl_2)$=53.6 ppm The two pure enantiomers of the diphosphine are recovered by means of decomplexation.

This is carried out especially using a hydrocyanic acid salt, preferably an alkali metal salt and particularly preferably the sodium salt, said salt being dissolved in the minimum amount of water necessary.

The complexes are solubilized in an organic solvent such as, for example, dichloromethane; the hydrocyanic acid salt, generally used in an excess of 2 to 5 mol per metal atom, is then introduced, with stirring.

The operation is again conducted under a controlled atmosphere and at room temperature.

The enantiomer is recovered from the organic phase, which is separated off, washed with water and dried, for example over sodium sulfate.

This gives the two enantiomers of bis[1-phospha-2,3-diphenyl-4,5-dimethylnorbornadiene], isolated pure, of the above-mentioned formulae [(Ia)—(S,S)-(+)] and [(Ib)—(R,R)-(−)], which have the following characteristics:

$^{31}$P NMR: $\delta(CDCl_3)$=−13.2 ppm−$[\alpha]_D$=+231° (c=1, $C_6D_6$)

$^{31}$P NMR: $\delta(CDCl_3)$=−13.2 ppm−$[\alpha]_D$=−198° (c=1, $C_6D_6$)

($[\alpha]_D$ being determined for a concentration of 10 mg/ml and at room temperature).

Continuing its researches, the Applicant found that the novel optically active diphosphines as mentioned above, in the form of metal complexes, could be used as catalysts for the asymmetric hydrogenation of ketonic compounds and derivatives.

The optically active diphosphines of formula (Ia) or (Ib) act as ligands in the formation of complexes with transition metals.

Said complexes comprise an optically active diphosphine and a transition metal and are characterized in that the ligand has one of the following formulae:

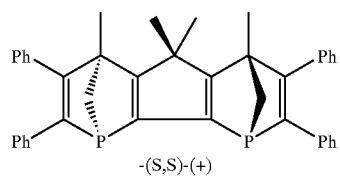

-(S,S)-(+)

(Ia)

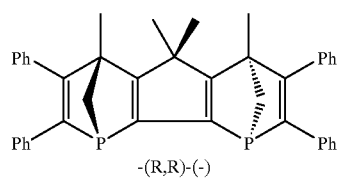

-(R,R)-(−)

(Ib)

Examples which may be mentioned of transition metals capable of forming complexes are especially metals such as rhodium, ruthenium, rhenium, iridium, cobalt, nickel, platinum and palladium.

Among the above-mentioned metals, rhodium, ruthenium and iridium are preferred.

Specific examples of said complexes of the present invention are given below without implying a limitation.

In said formulae, (P*P) represents the diphosphine of formula (Ia) or (Ib).

The rhodium and iridium complexes can be represented by the following formulae:

[ML₂(P*P)]Y      (IIa)

[ML₂(P*P)]Y      (IIb)

in which:
- (P*P) in formula (IIa) is the diphosphine of formula (Ia) and in formula (IIb) is the diphosphine of formula (Ib);
- M is rhodium or iridium;
- Y is an anionic coordinating ligand; and
- L is a neutral ligand.

The preferred rhodium or iridium complexes have formula (IIa) or (IIb) in which:
- L is an olefin having from 2 to 12 carbon atoms and two ligands L can be bonded together to form a polyunsaturated, linear or cyclic hydrocarbon chain, L preferably being 1,5-cyclooctadiene, norbornadiene or ethylene; and
- Y is the anion $PF_6^-$, $PCl_6^-$, $BF_4^-$, $BCl_4^-$, $SbF_6^-$, $SbCl_6^-$, $BPh_4^-$, $ClO_4^-$, $CN^-$ or $CF_3SO_3^-$, halogen, preferably $Cl^-$ or $Br^-$, a 1,3-diketonate, alkylcarboxylate or halogenoalkylcarboxylate anion with a lower alkyl radical, or a phenylcarboxylate or phenate anion whose benzene ring can be substituted by lower alkyl radicals and/or halogen atoms.

Lower alkyl radicals are generally understood as meaning linear or branched alkyl radicals having from 1 to 4 carbon atoms.

Other iridium complexes can be represented by the formulae

[IrL(P*P)]Y      (IIIa)

[IrL(P*P)]Y      (IIIb)

in which (P*P), L and Y are as defined for formulae (IIa) and (IIb).

As far as the ruthenium complexes are concerned, they preferably have the following formulae:

[RuY₁Y₂(P*P)]      (IVa)

[RuY₁Y₂(P*P)]      (IVb)

in which:
- (P*P) in formula (IVa) is the diphosphine of formula (Ia) and in formula (IVb) is the diphosphine of formula (Ib); and
- Y₁ and Y₂, which are identical or different, are preferably the anion $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$, a halogen atom, more particularly chlorine or bromine, or a carboxylate anion, preferably acetate or trifluoroacetate.

Other ruthenium complexes which can be used in the process of the invention have the formulae below:

[RuY₁Ar(P*P)Y₂]      (IVc)

[RuY₁Ar(P*P)Y₂]      (IVd)

in which:
- (P*P) in formula (IVc) is the diphosphine of formula (Ia) and in formula (IVd) is the diphosphine of formula (Ib);
- Ar is benzene, p-methylisopropylbenzene or hexamethylbenzene;
- Y₁ is a halogen atom, preferably chlorine or bromine; and
- Y₂ is an anion, preferably the anion $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$.

Complexes based on palladium and platinum can also be used in the process of the invention.

More specific examples of said complexes which may be mentioned, inter alia, are $PdCl_2(P*P)$ and $PtCl_2(P*P)$, in which (P*P) is the diphosphine of formula (Ia) or (Ib).

The complexes comprising the above-mentioned diphosphine and the transition metal can be prepared by the known processes described in the literature.

For the preparation of the ruthenium complexes, reference may be made especially to the publication by J.-P. Genêt [Acros Organics Acta 1, no. 1, pp. 1–8 (1994)], and for the other complexes reference may be made to the article by Schrock R. and Osborn J. A. [Journal of the American Chemical Society 93, p. 2397 (1971)].

They can be prepared in particular by reacting the diphosphine of formula (Ia) or (Ib) with the transition metal compound in an appropriate organic solvent.

The reaction is carried out at a temperature between room temperature (from 15 to 25° C.) and the reflux temperature of the reaction solvent.

Examples of organic solvents which may be mentioned, inter alia, are halogenated or non-halogenated aliphatic hydrocarbons, more particularly hexane, heptane, isooctane, decane, benzene, toluene, methylene chloride and chloroform; solvents of the ether or ketone type, especially diethyl ether, tetrahydrofuran, acetone and methyl ethyl ketone; and solvents of the alcohol type, preferably methanol or ethanol.

The metal complexes according to the invention, recovered by the conventional techniques (filtration or crystallization), are used in reactions for the asymmetric hydrogenation of substrates specified below.

A process for the asymmetric hydrogenation of a ketonic compound and derivative has now been found which is characterized in that the asymmetric hydrogenation of said compound is carried out in the presence of an effective amount of a metal complex comprising the optically active diphosphine of formula (Ia) or (Ib) as the ligand, and a transition metal; it is this discovery which forms the subject of the present invention.

More particularly, the ketonic compound or derivative has general formula (V):

(V)

in which:
- R₁ is different from R₂;
- R₁ and R₂ are a hydrocarbon radical having from 1 to 30 carbon atoms and optionally comprising one or more functional groups; or
- R₁ and R₂ can form a ring optionally comprising another heteroatom; and
- Z is or comprises an oxygen or nitrogen heteroatom or a functional group comprising at least one of these heteroatoms.

In formula (V), R₁ and R₂ are a substituted or unsubstituted, monovalent hydrocarbon radical which can be a linear or branched, saturated or unsaturated, acyclic aliphatic radical or a monocyclic or polycyclic, saturated, unsaturated or aromatic carbocyclic or heterocyclic radical.

$R_1$ and $R_2$ can have a variety of meanings. Different examples are given below without in any way implying a limitation.

In the compounds of formula (V), $R_1$ and $R_2$ are a linear or branched, saturated or unsaturated, acyclic aliphatic radical.

More precisely, $R_1$ and $R_2$ are a linear or branched, acyclic aliphatic radical preferably having from 1 to 12 carbon atoms, which is saturated or comprises one or more units of unsaturation in the chain, generally 1 to 3 units of unsaturation, which can be simple or conjugated double bonds, or triple bonds.

The hydrocarbon chain can optionally:
be interrupted by one of the following groups W:
—O—; —CO—; —COO—; —NT—; —CO—NT—; —S—; —SO$_2$—; —NT—CO—;
in which T is a hydrogen atom or a linear or branched alkyl group having from 1 to 6 carbon atoms, preferably a methyl or ethyl radical;
and/or carry one of the following substituents:
—OH; —COOH; —COOX; —CO—N(T)(T); —COOT; —CHO; —COT; —NO$_2$; —X; —CF$_3$;
in which the radicals T are identical or different and X is a halogen atom.

$R_1$ and $R_2$ can also be a linear or branched, saturated or unsaturated, acyclic aliphatic radical optionally carrying a cyclic substituent. Ring is understood as meaning a saturated, unsaturated or aromatic carbocyclic or heterocyclic ring.

The acyclic aliphatic radical can be joined to the ring by a valence bond or by one of the groups W mentioned above.

Examples of cyclic substituents which can be considered are cycloaliphatic, aromatic or heterocyclic substituents, especially cycloaliphatic substituents comprising 6 carbon atoms in the ring, or benzene substituents, these cyclic substituents themselves optionally carrying one or more substituents.

The benzyl radical, inter alia, may be mentioned as an example of such radicals.

In general formula (I), $R_1$ and $R_2$ can also be a monocyclic carbocyclic radical which is saturated or comprises 1 or 2 units of unsaturation in the ring and which generally has from 3 to 7 carbon atoms, preferably 5 or 6 carbon atoms, in the ring.

Cyclopentyl or cyclopentenyl and cyclohexyl or cyclohexenyl radicals may be mentioned as preferred examples of radicals R.

In the case where $R_1$ and $R_2$ are a saturated or unsaturated, monocyclic carbocyclic radical, it is possible for one or more of the ring carbon atoms to be replaced by a heteroatom, preferably oxygen, nitrogen or sulfur, or by a functional group, preferably carbonyl or ester, to give a monocyclic heterocyclic compound. The number of atoms in the ring can vary widely from 3 to 8 atoms, but is preferably equal to 5 or 6 atoms.

The radicals $R_1$ and $R_2$ can also be polycyclic, preferably bicyclic, carbocyclic radicals, meaning that at least two rings share two carbon atoms. In the case of polycyclic radicals, the number of carbon atoms in each ring varies between 3 and 6, the total number of carbon atoms preferably being equal to 7.

Examples of commonly encountered bicyclic structures are given below:

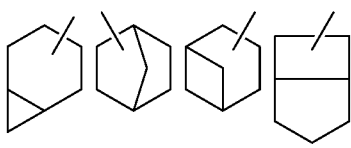

[4,1,0]    [2,2,1]    [3,1,1]    [3,2,0]

The radicals $R_1$ and $R_2$ can also be polycyclic, preferably bicyclic, heterocyclic radicals, meaning that at least two rings share two atoms. In this case, the number of atoms in each ring varies between 3 and 6 and is more preferably equal to 5 or 6.

The radicals $R_1$ and $R_2$ can preferably be aromatic carbocyclic radicals, especially benzene radicals of the general formula

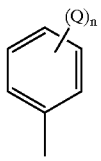

in which:

n is an integer from 0 to 5, preferably from 0 to 3; and
Q is R or one of the following groups or functional groups:
a linear or branched alkyl radical having from 1 to 6 carbon atoms, preferably from 1 to 4 carbon atoms, such as methyl, ethyl, propyl, isopropyl, butyl, isobutyl, sec-butyl or tert-butyl;
a linear or branched alkenyl radical having from 2 to 6 carbon atoms, preferably from 2 to 4 carbon atoms, such as vinyl or allyl; or
a radical of the formula
—R$_3$—OH
—R$_3$—O—R$_4$
—R$_3$—CO—R$_4$
—R$_3$—COOR$_4$
—R$_3$—CHO
—R$_3$—NO$_2$
—R$_3$—CN
—R$_3$—N(R$_4$)$_2$
—R$_3$—CO—N(R$_4$)$_2$
—R$_3$—PO—(OR$_4$)$_2$
—R$_3$—SH
—R$_3$—X
—R$_3$—CF$_3$
in which $R_3$ is a valence bond or a saturated or unsaturated, linear or branched, divalent hydrocarbon radical having from 1 to 6 carbon atoms, such as, for example, methylene, ethylene, propylene, isopropylene or isopropylidene; the radicals $R_4$, which are identical or different, are a hydrogen atom, a linear or branched alkyl radical having from 1 to 6 carbon atoms, a benzyl radical or a phenyl radical; and X symbolizes a halogen atom, preferably a chlorine, bromine or fluorine atom; or Q is R' or one of the following, more complex radicals:

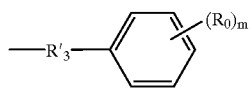

in which:
m is an integer from 0 to 5, preferably from 0 to 3;
$R_0$ is as defined above for R; and
$R'_3$ is a valence bond, a saturated or unsaturated, linear or branched, divalent hydrocarbon group having from 1 to 6 carbon atoms, such as, for example, methylene, ethylene, propylene, isopropylene or isopropylidene, or one of the following groups:
—O—; —CO—; —COO—; —NR$_4$—; —CO—NR$_4$—; —S—; —SO$_2$—; —NR$_4$—CO—;
in which $R_4$ is as defined above.

More precise examples which may be mentioned of radicals $R_1$ and $R_2$ of formula (II) are phenyl, tolyl, xylyl, 1-methoxyphenyl and 2-nitrophenyl radicals and biphenyl, 1,1'-methylenebiphenyl, 1,1'-isopropylidenebiphenyl, 1,1'-carboxybiphenyl, 1,1'-oxybiphenyl and 1,1'-iminobiphenyl radicals, it being possible for said radicals to be substituted by one or more radicals R as defined above.

$R_1$ and $R_2$ can also be a polycyclic aromatic hydrocarbon radical, it being possible for the rings together to form ortho-fused or ortho- and peri-fused systems. A naphthalene radical may be mentioned more particularly.

In general formula (I), $R_1$ and $R_2$ can also be a saturated, unsaturated or aromatic heterocyclic radical containing especially 5 or 6 atoms in the ring, including 1 or 2 heteroatoms such as nitrogen, sulfur and oxygen atoms.

$R_1$ and $R_2$ can also be a polycyclic aromatic heterocyclic radical defined as being either a radical consisting of at least 2 aromatic or non-aromatic heterocycles containing at least one heteroatom in each ring and together forming ortho-fused or ortho- and peri-fused systems, or a radical consisting of at least one aromatic or non-aromatic hydrocarbon ring and at least one aromatic or non-aromatic heterocycle together forming ortho-fused or ortho- and peri-fused systems.

It should be noted that if the radicals $R_1$ and $R_2$ comprise any kind of ring, it is possible for this ring to carry a substituent. The substituent is of an arbitrary nature provided that it does not interfere with the desired product. R illustrates the types of substituents commonly encountered. The substituents most frequently carried by the ring are one or more alkyl or alkoxy radicals preferably having from 1 to 4 carbon atoms, or a halogen atom.

The preferred compounds of formula (V) have a phenyl radical as the radical $R_1$ or $R_2$.

In formula (V), $R_1$ and $R_2$ can together form, with the carbon atom carrying the functional group, a monocyclic or polycyclic ring system.

Thus the compound of formula (V) can be:
a saturated or unsaturated, monocyclic carbocyclic compound;
a polycyclic compound comprising at least two saturated and/or unsaturated carbocycles;
a compound comprising at least two saturated and/or unsaturated rings, it being possible for one or more of the carbon atoms to be replaced by a heteroatom; or
a polycyclic compound comprising at least two carbocycles, one of which is aromatic.

In the case of a monocyclic compound, the number of carbon atoms in the ring can vary widely from 3 to 20 carbon atoms, but is preferably 5 or 6 carbon atoms.

The carbocycle can be saturated or comprise 1 or 2 units of unsaturation in the ring, preferably 1 or 2 double bonds which are most frequently in the α-position to the functional group.

The compound can also be polycyclic, preferably bicyclic, meaning that at least two rings share two carbon atoms.

In the case of polycyclic compounds, the number of carbons in each ring is smaller, generally from 3 to 8 but preferably equal to 5 or 6 carbon atoms.

The polycyclic compound can comprise at least two saturated and/or unsaturated rings, it being possible for one or more (preferably two) of the carbon atoms to be replaced by a heteroatom, preferably an oxygen or nitrogen atom.

The polycyclic compound can comprise at least two carbocycles, one of which is aromatic, the aromatic ring preferably being a benzene ring.

The ring or rings can carry one or more substituents.

The number of substituents present on the ring depends on the number of carbons in the ring and on the presence or absence of units of unsaturation in the ring.

The maximum number of substituents capable of being carried by a ring is easily determined by those skilled in the art.

As regards the nature of the substituents, examples of substituents are given above for R, but this list does not imply a limitation.

More precisely, if the compound of formula (V) is a saturated, monocyclic carbocyclic compound, the number of carbon atoms in the ring can vary widely from 3 to 20 carbon atoms, but is preferably 5 or 6 carbon atoms. One or two functional groups (C═Z) may be present on the ring. The functional group is preferably carried by a saturated carbocycle having 5 or 6 carbon atoms.

The saturated carbocycle can carry substituents. The number of substituents on each ring can vary widely from 1 to 5. It is generally 1 or 2.

The carbocycle can be unsaturated and comprise 1 or 2 units of unsaturation in the ring, preferably 1 or 2 double bonds which are most frequently in the α-position to the functional group. It comprises from 4 to 20 carbon atoms. One or two functional groups may be present on the ring. The functional group is preferably carried by an unsaturated carbocycle having 5 or 6 carbon atoms.

The unsaturated carbocycle can carry substituents. The number of substituents on each ring can vary widely from 1 to 5. It is generally 1 or 2.

The compound can also be polycyclic, preferably bicyclic.

The polycyclic compound can comprise at least two saturated and/or unsaturated rings, it being possible for one or more (preferably two) of the carbon atoms to be replaced by a heteroatom, preferably an oxygen or nitrogen atom.

The polycyclic, preferably bicyclic, carbocyclic compound can comprise two saturated carbocycles, each preferably having from 4 to 8 carbon atoms. A functional group may be present on one or both rings. There may also be two functional groups on the same ring. The functional group is preferably carried by one or two saturated carbocycles having 5 or 6 carbon atoms.

In these polycyclic compounds, one or more carbon atoms (preferably two) can be replaced by a heteroatom, preferably a nitrogen or oxygen atom.

The ring or rings of these polycyclic compounds can carry substituents. The number of substituents on each ring is generally 1 to 4, preferably 1 or 2.

The cyclic compound can be a bicyclic carbocyclic compound comprising two carbocycles, each preferably having from 4 to 7 carbon atoms and the one being saturated and the other unsaturated, generally with only one double bond. The functional group can be present either on the saturated ring or on the unsaturated ring, or on both. The functional group is preferably carried by a saturated or unsaturated carbocycle having 5 or 6 carbon atoms.

The ring or rings of these polycyclic compounds can carry substituents. The number of substituents on each ring is generally 1 to 3, preferably 1 or 2.

The polycyclic, preferably bicyclic, carbocyclic compound can comprise two unsaturated carbocycles, each preferably having 5 or 6 carbon atoms. A functional group may be present on one of the two rings.

In these polycyclic compounds, one or more carbon atoms (preferably two) can be replaced by a heteroatom, preferably a nitrogen or oxygen atom.

The ring or rings of these polycyclic compounds can carry substituents. The number of substituents on each ring is generally 1 to 4, preferably 1 or 2.

The polycyclic carbocyclic compound can comprise it least one aromatic carbocycle, preferably a benzene ring, and a carbocycle preferably having from 4 to 7 carbon atoms and comprising one or two functional groups.

The polycyclic compound is preferably a bicyclic compound comprising a benzene ring and a carbocycle of 5 or 6 carbon atoms, comprising one or two functional groups.

The two rings of this bicyclic radical can carry substituents. The number of substituents on each ring is generally 1 to 4, preferably 1 or 2.

More precisely, the compound of formula (V) corresponds to a ketonic compound of formula (Va):

(Va)

in which:
R$_1$ is different from R$_2$, the radicals R$_1$ and R$_2$ being a hydrocarbon radical having from 1 to 30 carbon atoms and optionally comprising another ketone group and/or an acid, ester, thioacid or thioester group; or
R$_1$ and R$_2$ can form a substituted or unsubstituted carbocyclic or heterocyclic ring having 5 or 6 atoms.

A first class of substrates to which the process of the invention more preferably applies consists of optionally functionalized ketones.

The latter term is understood as meaning the presence of any functional group in the α-, β-, γ- or δ-position, with the exception of any group comprising a carbonyl group.

Said ketones can be symbolized by the following chemical formula:

(Va$_1$)

in which
R$_1$ and R$_2$ are:
a linear or branched alkyl radical having from 1 to 12 carbon atoms, preferably from 1 to 4 carbon atoms, such as methyl, ethyl, propyl, isopropyl, butyl, isobutyl, sec-butyl or tert-butyl;
an alkenyl radical having from 2 to 12 carbon atoms, preferably an allyl radical;
an optionally substituted phenyl, naphthyl or benzyl radical;
a triphenylmethyl radical; or
a radical of the formula
—R$_3$—OH
—R$_3$—O—R$_4$
—R$_3$—CO—R$_4$
—R$_3$—COOR$_4$
—R$_3$—CHO
—R$_3$—NO$_2$
—R$_3$—CN
—R$_3$—N(R$_4$)$_2$
—R$_3$—CO—N(R$_4$)$_2$
—R$_3$—PO—(OR$_4$)$_2$
—R$_3$—SH
—R$_3$—X
—R$_3$—CF$_3$ in which R$_3$ is a valence bond or a saturated or unsaturated, linear or branched, divalent hydrocarbon radical having from 1 to 6 carbon atoms, such as, for example, methylene, ethylene, propylene, isopropylene or isopropylidene; the radicals R$_4$, which are identical or different, are a hydrogen atom, a linear or branched alkyl radical having from 1 to 6 carbon atoms, a benzyl radical or a phenyl radical; and X symbolizes a halogen atom, preferably a chlorine, bromine or fluorine atom; or
R$_1$ and R$_2$ can form a substituted or unsubstituted carbocyclic or heterocyclic ring having 5 or 6 atoms.

If the radical or radicals R$_1$ and R$_2$ have a hydrocarbon chain, this can optionally be interrupted by a heteroatom (for example oxygen or nitrogen) or by a functional group, and/or can optionally carry a substituent (for example a halogen, a trifluoromethyl group or an ester group).

In the case where the radical or radicals R$_1$ and R$_2$ have a ring such as a benzene ring or the like, there can be substituents on this ring. The substituent present can be of any type and reference may be made to the meanings of R. It is most frequently a lower alkyl radical, a lower alkoxy radical, a hydroxyl group and/or a halogen atom, especially a fluorine or chlorine atom.

The following may be mentioned, inter alia, as examples of ketones of formula (Va$_1$):

methyl phenyl ketone,
isopropyl phenyl ketone,
cyclopropyl phenyl ketone,
allyl phenyl ketone,
p-methylphenyl methyl ketone, benzyl phenyl ketone,
phenyl triphenylmethyl ketone,
o-bromoacetophenone,
α-bromoacetone,
α-dibromoacetone,
α-chloroacetone,
α-dichloroacetone,
α-trichloroacetone,
1-chloro-3,3-dichloroacetone,
1-chloro-2-oxobutane,
1-fluoro-2-oxobutane,
1-chloro-3-methyl-2-butanone,
α-chloroacetophenone,
1-chloro-3-phenylacetone,
α-methylaminoacetone,
α-dimethylaminoacetone,
1-butylamino-2-oxopropane,
1-dibutylamino-2-oxopropane,
1-methylamino-2-oxobutane,
1-dimethylamino-2-oxobutane,
1-dimethylamino-3-methyl-2-oxobutane,
1-dimethylamino-2-oxopentane,
α-dimethylaminoacetophenone,
α-hydroxyacetone,
1-hydroxy-3-methyl-2-butanone,
1-hydroxy-2-oxobutane,
1-hydroxy-2-oxopentane,
1-hydroxy-2-oxohexane,
1-hydroxy-2-oxo-3-methylbutane,
α-hydroxyacetophenone,
1-hydroxy-3-phenylacetone,
α-methoxyacetone,
α-methoxyacetophenone,
α-ethoxyacetone,
α-butoxyacetophenone,
α-chloro-p-methoxyacetophenone,
α-naphthenone,
1-ethoxy-2-oxobutane,
1-butoxy-2-oxobutane,
α-dimethoxyphosphorylacetone,
3-oxotetrahydrothiophene.

The invention is also perfectly applicable to the hydrogenation of diketonic compounds which have a carbonyl group in the α-, β-, γ- or δ-position relative to a first carbonyl group. More particularly, the diketonic compounds have formula (Va$_2$):

$$\underset{R_1}{\overset{O}{\|}}{\overset{}{C}}-\left[\underset{R_4}{\overset{R_3}{C}}\right]_m-\underset{}{\overset{O}{\|}}{C}-R_2 \qquad (Va_2)$$

in which:
  m is equal to 0, 1, 2 or 3 and is preferably equal to 0 or 1;
  the radicals $R_1$ and $R_2$, which are different, are:
    a linear or branched alkyl radical having from 1 to 12 carbon atoms, optionally substituted with a halogen atom, preferably from 1 to 4 carbon atoms, such as methyl, ethyl, propyl, isopropyl, butyl, isobutyl, sec-butyl or tert-butyl;
    an alkenyl radical having from 2 to 12 carbon atoms, preferably an allyl radical;
    an optionally substituted phenyl, naphthyl or benzyl radical; or
    a radical of the formula
      —$R_5$—OH
      —$R_5$—O—$R_6$
      —$R_5$—CO—$R_6$
      —$R_5$—COO$R_6$
      —$R_5$—N($R_6$)$_2$
      —$R_5$—CO—N($R_6$)$_2$
      —$R_5$—PO—(O$R_6$)$_2$
      —$R_5$—SH
      —$R_5$—X
      —$R_5$—CF$_3$
    in which $R_5$ is a valence bond or a saturated or unsaturated, linear or branched, divalent hydrocarbon radical having from 1 to 6 carbon atoms, such as, for example, methylene, ethylene, propylene, isopropylene or isopropylidene; the radicals $R_6$, which are identical or different, are a hydrogen atom, a linear or branched alkyl radical having from 1 to 6 carbon atoms, a benzyl radical or a phenyl radical; and X symbolizes a halogen atom, preferably a chlorine, bromine or fluorine atom; or
    one of the radicals $R_1$ and $R_2$ can be a hydrogen atom; and
    the radicals $R_3$ and $R_4$, which are identical or different, are:
      a hydrogen atom;
      a linear or branched alkyl radical having from 1 to 12 carbon atoms, preferably from 1 to 4 carbon atoms, such as methyl, ethyl, propyl, isopropyl, butyl, isobutyl, sec-butyl or tert-butyl;
      a halogen atom; or
      a group of the type —$R_5$—COO$R_6$, in which $R_5$ and $R_6$ are as defined above; or
    $R_1$ or $R_2$ and $R_3$ or $R_4$ can form a substituted or unsubstituted carbocyclic or heterocyclic ring having 5 or 6 atoms.

If the radical or radicals $R_1$ and $R_2$ have a hydrocarbon chain, this can optionally be interrupted by a heteroatom (for example oxygen or nitrogen) or by a functional group, and/or can optionally carry a substituent (for example a halogen, a trifluoromethyl group or an ester group).

In the case where the radical or radicals $R_1$ and $R_2$ have a ring, they can be substituted as described for formula (Va$_1$).

The following may be mentioned in particular as examples of diketonic compounds of formula (Va$_2$):

α-formylacetone,
diacetyl,
3,4-dioxohexane,
4,5-dioxooctane,
1-phenyl-1,2-dioxopropane,
1-phenyl-2,3-dioxobutane,
dibenzoyl,
p-methoxydibenzoyl,
1,2-cyclopentanedione,
1,2-cyclohexanedione,
acetylacetone,
3,5-heptanedione,
4,6-nonanedione,
5,7-undecanedione,
2,4-hexanedione,
2,4-heptanedione,
2,4-octanedione,
2,4-nonanedione,
3,5-nonanedione, 3,5-decanedione,
2,4-dodecanedione,
1-phenyl-1,3-butanedione,
1-phenyl-1,3-pentanedione,
1-phenyl-1,3-hexanedione,
1-phenyl-1,3-heptanedione,
3-methyl-2,4-pentanedione,
1,3-diphenyl-1,3-propanedione,
1,5-diphenyl-2,4-pentanedione,
1,3-di(trifluoromethyl)-1,3-propanedione,
3-chloro-2,4-pentanedione,
1,5-dichloro-2,4-pentanedione,
1,5-dihydroxy-2,4-pentanedione,
1,5-dibenzyloxy-2,4-pentanedione,
1,5-diamino-2,4-pentanedione,
1,5-di(methylamino)-2,4-pentanedione,
1,5-di(dimethylamino)-2,4-pentanedione,
methyl 3,5-dioxohexanoate,
3-carbomethoxy-2,4-pentanedione,
3-carboethoxy-2,4-pentanedione,
1,3-cyclopentanedione,
1,3-cyclohexanedione,
1,3-cycloheptanedione,
5-carboethoxy-1,3-cyclopentanedione,
2-acetyl-1-cyclopentanone,
2-acetyl-1-cyclohexanone.

The invention is also perfectly applicable to the hydrogenation of keto acids or derivatives and keto thioacids or derivatives with a functional group (acid, ester, thioacid or thioester) in the α-, β-, γ- or δ-position relative to the carbonyl group. The invention is perfectly suitable for the hydrogenation of the compounds of formula ($Va_3$) or ($Va_4$):

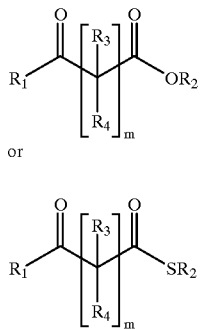

in which:
  m is equal to 0, 1, 2 or 3 and is preferably equal to 0 or 1;
  the radical $R_1$ is:
    a linear or branched alkyl radical having from 1 to 12 carbon atoms, preferably from 1 to 4 carbon atoms, such as methyl, ethyl, propyl, isopropyl, butyl, isobutyl, sec-butyl or tert-butyl;
    an alkenyl radical having from 2 to 12 carbon atoms, preferably an allyl radical;
    an optionally substituted phenyl, naphthyl or benzyl radical; or
    a radical of the formula
  —$R_5$—OH
  —$R_5$—O—$R_6$
  —$R_5$—CO—$R_6$
  —$R_5$—COO$R_6$
  —$R_5$—N($R_6$)$_2$
  —$R_5$—CO—N($R_6$)$_2$
  —$R_5$—PO—(O$R_6$)$_2$
  —$R_5$—SH
  —$R_5$—X
  —$R_5$—CF$_3$
  in which $R_5$ is a valence bond or a saturated or unsaturated, linear or branched, divalent hydrocarbon radical having from 1 to 6 carbon atoms, such as, for example, methylene, ethylene, propylene, isopropylene or isopropylidene; the radicals $R_6$, which are identical or different, are a hydrogen atom, a linear or branched alkyl radical having from 1 to 6 carbon atoms, a benzyl radical or a phenyl radical; and X symbolizes a halogen atom, preferably a chlorine, bromine or fluorine atom;
  the radical $R_2$ is:
    a hydrogen atom;
    a linear or branched alkyl radical having from 1 to 6 carbon atoms, preferably from 1 to 4 carbon atoms, such as methyl, ethyl, propyl, isopropyl, butyl, isobutyl, sec-butyl or tert-butyl;
    a benzyl radical; or
    a phenyl radical; and
  the radicals $R_3$ and $R_4$, which are identical or different, are:
    a hydrogen atom;
    a linear or branched alkyl radical having from 1 to 12 carbon atoms, preferably from 1 to 4 carbon atoms, such as methyl, ethyl, propyl, isopropyl, butyl, isobutyl, sec-butyl or tert-butyl;
    a halogen atom;
    a group of the type —$R_5$—COO$R_6$, in which $R_5$ and $R_6$ are as defined above; or
    a group of the type —$R_5$—CO—N($R_6$)$_2$, in which $R_5$ and $R_6$ are as defined above; or
  $R_1$ and $R_2$ or $R_1$ and $R_3$ or $R_1$ and $R_4$ or $R_2$ and $R_4$ can form a substituted or unsubstituted carbocyclic or heterocyclic ring having 5 or 6 atoms.

If the radical or radicals $R_1$ and $R_2$ have a hydrocarbon chain, this can optionally be interrupted by a heteroatom (for example oxygen or nitrogen) or by a functional group, and/or can optionally carry a substituent (for example a halogen, a trifluoromethyl group or an ester group).

In the case where the radical or radicals $R_1$ and $R_2$ have a ring, they can be substituted as described for formula ($Va_1$).

The following may be mentioned as more particular examples of compounds of formula ($Va_3$) or ($Va_4$):

2-acetylbenzoic acid,
pyruvic acid,
2-oxobutanoic acid,
3-methyl-2-oxobutanoic acid,
phenylglyoxylic acid,
phenylpyruvic acid,
p-methoxyphenylpyruvic acid,
3,4-dimethoxyphenylpyruvic acid,
methyl acetoacetate,
ethyl acetoacetate,
n-propyl acetoacetate,
isopropyl acetoacetate,
n-butyl acetoacetate,
t-butyl acetoacetate,
n-pentyl acetoacetate,
n-hexyl acetoacetate,
n-heptyl acetoacetate, n-octyl acetoacetate,
methyl 3-oxopentanoate,
methyl 3-oxohexanoate,
methyl 3-oxoheptanoate,
ethyl 3-oxooctanoate,
ethyl 3-oxononanoate,
ethyl 3-oxodecanoate,
ethyl 3-oxoundecanoate,
ethyl 3-oxo-3-phenylpropionate,
ethyl 4-phenyl-3-oxobutanoate,
methyl 5-phenyl-3-oxopentanoate,
ethyl 3-oxo-3-p-methoxyphenylpropionate,
methyl 4-chloroacetoacetate,
ethyl 4-chloroacetoacetate,
methyl 4-fluoroacetoacetate,
ethyl 3-trifluoromethyl-3-oxopropionate,
ethyl 4-hydroxy-3-oxobutanoate,
methyl 4-methoxyacetoacetate,
methyl 4-tert-butoxyacetoacetate,
methyl 4-benzyloxy-3-oxobutanoate,
ethyl 4-benzyloxy-3-oxobutanoate,
methyl 4-amino-3-oxobutanoate,
ethyl 3-methylamino-3-oxobutanoate,
methyl 4-dimethylamino-3-oxobutanoate,
ethyl 4-dimethylamino-3-oxobutanoate,
methyl 2-methylacetoacetate,
ethyl 2-methylacetoacetate,
ethyl 2-chloroacetoacetate,
diethyl 2-acetylsuccinate,
diethyl 2-acetylglutarate,
dimethyl acetylmalonate,
thiomethyl acetoacetate,
thioethyl acetoacetate,
thiophenyl acetoacetate,
methyl pyruvate,
ethyl 3-methyl-2-oxobutanoate,
ethyl phenylglyoxylate,
methyl phenylpyruvate,
ethyl phenylpyruvate,
3-oxobutanoic dimethylamide,
3-oxobutanoic benzylamide,
2-carboethoxycyclopentanone,
2-carboethoxycyclohexanone,
ketopentalactone,
4-oxopentanoic acid,
4-oxohexanoic acid,
4-oxoheptanoic acid,
4-oxodecanoic acid,
4-oxododecanoic acid,
4-phenyl-4-oxybutyric acid,
4-p-methoxyphenyl-4-oxybutyric acid,
4-(3,4-dimethoxyphenyl)-4-oxobutyric acid,
4-(3,4,5-trimethoxyphenyl)-4-oxobutyric acid,
4-p-chlorophenyl-4-oxybutyric acid,
4-phenyl-4-oxobutyric acid.

It should be noted that if the asymmetric hydrogenation is to be carried out on a γ-keto acid or derivative, the product obtained is generally a γ-butyrolactone derivative or, in the case of a δ-keto acid, a valerolactone derivative.

Other examples of ketones which may be mentioned, inter alia, are the following saturated or unsaturated, monocyclic or polycyclic ketonic compounds:

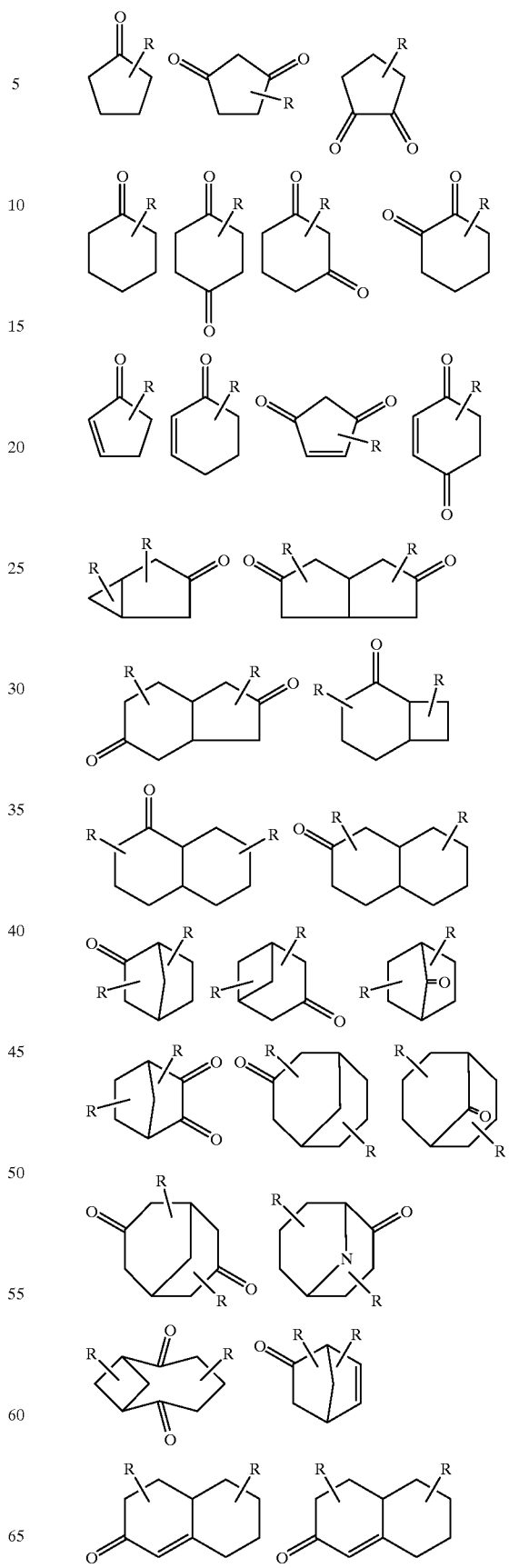

-continued

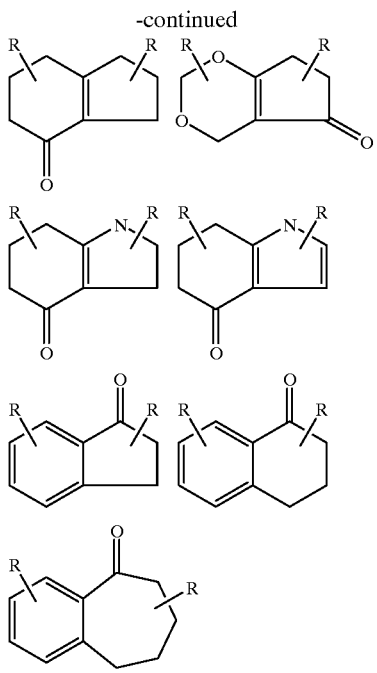

It is also possible to use ketones of the steroid type (for example 3-cholestanone, 5-cholesten-3-one):

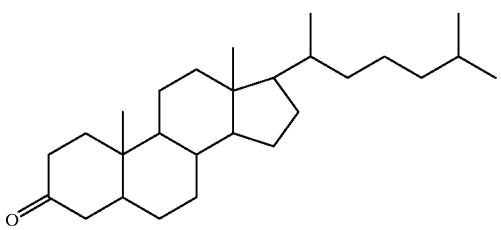

Another class of substrates to which the process of the invention applies consists of the compounds of formula (V) in which Z symbolizes a nitrogen atom or a functional group comprising a nitrogen atom, and which have formula (Vb):

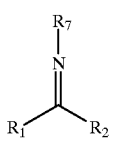

(Vb)

in which:

$R_1$ and $R_2$, which are different, are as defined above; and $R_7$ is:
- a hydrogen atom;
- a hydroxyl group;
- a group $OR_8$;
- a hydrocarbon radical $R_8$;

a group of the formula

or a group of the formula

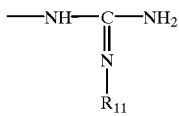

where $R_8$, $R_9$, $R_{10}$ and $R_{11}$ are a hydrogen atom or a hydrocarbon group having from 1 to 30 carbon atoms.

It should be noted that the invention also includes substrates which comprise several functional groups defined above and which can be derivatives of diketonic compounds, the functional groups being in the α-, β-, γ- or δ-position.

More particularly, the compounds which are preferably used in the process of the invention have the following formulae:

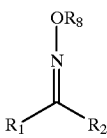
(Vb$_1$)

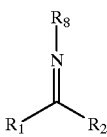
(Vb$_2$)

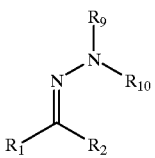
(Vb$_3$)

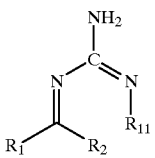
(Vb$_4$)

in which:
the radicals $R_1$, $R_2$ and $R_8$ to $R_{11}$ are:
- a linear or branched alkyl radical having from 1 to 12 carbon atoms;
- a cycloalkyl radical having from 5 to 12 carbon atoms;
- an aryl radical having from 6 to 12 carbon atoms;
- an aralkyl radical having from 7 to 12 carbon atoms;
- an aryl radical having from 6 to 12 carbon atoms carrying substituents such as an alkyl or alkoxy radical having from 1 to 4 carbon atoms, an amino, ($C_1$–$C_4$)alkylamino or di($C_1$–$C_4$)alkylamino group, a nitro group, a halogen atom or a ($C_1$–$C_4$) alkoxycarbonyl group;

an aryl radical having from 6 to 12 carbon atoms;

a saturated or unsaturated heterocyclic radical;

an alkanoyl radical having from 1 to 12 carbon atoms;

an arylcarbonyl radical having from 6 to 12 carbon atoms; or an arylalkanoyl radical having from 6 to 12 carbon atoms; or $R_1$ and $R_2$, $R_1$ and $R_8$, $R_2$ and $R_8$, $R_1$ and $R_9$, $R_2$ and $R_{10}$, $R_1$ and $R_{11}$ or $R_2$ and $R_{11}$ can form a substituted or unsubstituted, monocyclic or polycyclic carbocyclic or heterocyclic ring having 5 or 6 atoms in each ring.

In formulae ($Vb_1$) to ($Vb_4$), the radicals $R_1$, $R_2$ and $R_8$ to $R_{11}$, which are identical or different, are preferably:

a linear or branched alkyl radical having from 1 to 4 carbon atoms;

a cyclopentyl or cyclohexyl radical;

a phenyl radical;

a benzyl or phenylethyl radical;

a phenyl radical carrying substituents such as an alkyl or alkoxy radical having from 1 to 4 carbon atoms, an amino, ($C_1$–$C_4$)alkylamino or di($C_1$–$C_4$)alkylamino group, a nitro group, a halogen atom or a ($C_1$–$C_4$) alkoxycarbonyl group;

a naphthyl radical;

a saturated or unsaturated, oxygen-containing or nitrogen-containing heterocyclic radical having 5 or 6 atoms;

an acetyl radical or a benzoyl radical; or an arylalkanoyl radical having from 6 to 12 carbon atoms.

The compounds of formula ($Vb_1$) are of the oxime type. An example which may be mentioned, inter alia, is acetophenone oxime:

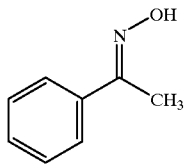

The compounds of formula ($Vb_2$) are imines. The following may be mentioned as more specific examples:
as N-alkylketoimines
  N-isobutyl-2-iminopropane
  N-isobutyl-1-methoxy-2-iminopropane
as N-arylalkylketoimines
  N-benzyl-1-imino-1-(phenyl)ethane
  N-benzyl-1-imino-1-(4-methoxyphenyl)ethane
  N-benzyl-1-imino-1-(2-methoxyphenyl)ethane
as N-arylketoimines
  N-phenyl-2-iminopentane
  N-(2,6-dimethylphenyl)-2-iminopentane
  N-(2,4,6-trimethylphenyl)-2-iminopentane
  N-phenyl-1-imino-1-phenylethane
  N-phenyl-1-methoxy-2-iminopropane
  N-(2,6-dimethylphenyl)-1-methoxy-2-iminopropane
  N-(2-methyl-6-ethylphenyl)-1-methoxy-2-iminopropane As regards the compounds of formula ($Vb_3$), these are compounds of the hydrazone type which are optionally N-acylated or N-benzoylated, and the following may be mentioned more particularly:

1-cyclohexyl-1-(2-benzoylhydrazono)ethane,
1-phenyl-1-(2-benzoylhydrazono)ethane,
1-p-methoxyphenyl-1-(2-benzoylhydrazono)ethane,
1-p-ethoxyphenyl-1-(2-benzoylhydrazono)ethane,
1-p-nitrophenyl-1-(2-benzoylhydrazono)ethane,
1-p-bromophenyl-1-(2-benzoylhydrazono)ethane,
1-p-carboethoxyphenyl-1-(2-benzoylhydrazono)ethane,
1,2-diphenyl-1-(2-benzoylhydrazono)ethane,
3-methyl-2-(2-p-dimethylaminobenzoylhydrazono)butane,
1-phenyl-1-(2-p-methoxybenzoylhydrazono)ethane,
1-phenyl-1-(2-p-dimethylaminobenzoylhydrazono)ethane,
ethyl 2-(2-benzoylhydrazono)propionate,
methyl 2-(2-benzoylhydrazono)butyrate,
methyl 2-(2-benzoylhydrazono)valerate,
methyl 2-phenyl-2-(2-benzoylhydrazono)acetate.

The invention also includes the semicarbazones of formula ($Vb_4$).

Starting substrates which may also be mentioned are cyclic ketoimines with an endocyclic or exocyclic bond, and more particularly:

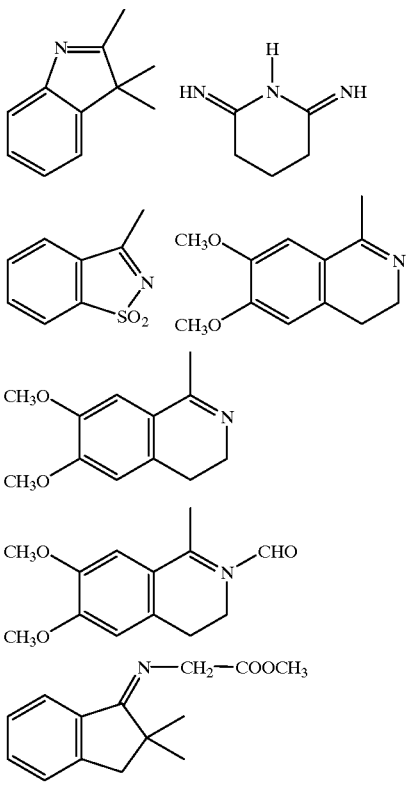

In the process of the invention, the selective asymmetric hydrogenation is carried out using, as catalysts, the metal complexes of the invention containing the optically active diphosphines of general formula (Ia) or (Ib) as ligands.

When the invention applies more precisely to ketonic compounds and more particularly to the compounds of formula (Va), the preferred choice is to use diphosphine/ruthenium complexes. In the case where the substrate is of the nitrogen-containing type (Vb), especially an imine, diphosphine/rhodium or iridium complexes, and more preferably phosphine/iridium complexes, are used.

By choosing one of the optical isomers of the diphosphine, having the (+) or (−) optical rotation, and using a diphosphine/transition metal complex comprising the chosen isomer, the ketonic compound or derivative is hydrogenated to give a compound with the desired absolute configuration.

The hydrogenation is generally carried out at a temperature between 20 and 100° C.

The hydrogen pressure can be between 0.1 and 200 bar and more preferably between 1 and 150 bar.

The diphosphine/transition metal complex is used in such a way that the ratio of the number of metal atoms present in the complex to the number of mol of compound to be hydrogenated is between 0.1 and 0.0001.

The hydrogenation process is preferably carried out in an organic solvent. Any solvent is used provided that it is stable under the reaction conditions.

It is preferable to choose a polar organic solvent and more particularly the following solvents:

aliphatic, cycloaliphatic or aromatic ethers and more particularly diethyl ether, dipropyl ether, diisopropyl ether, dibutyl ether, methyl tert-butyl ether, ditert-butyl ether, ethylene glycol dimethyl ether, diethylene glycol dimethyl ether, diphenyl ether, dibenzyl ether, anisole, phenetole, 1,4-dimethoxybenzene, veratrole, 1,4-dioxane and tetrahydrofuran (THF);

monohydric or polyhydric alcohols and more particularly aliphatic monoalcohols such as methanol, ethanol, propanol, butanol, sec-butanol, tert-butanol, pentanol and hexanol; aliphatic dialcohols such as ethylene glycol, diethylene glycol and propylene glycol; and cycloaliphatic alcohols such as cyclopentanol and cyclohexanol;

aliphatic ketones such as acetone, methyl ethyl ketone and diethyl ketone; and aliphatic esters such as, in particular, methyl acetate, ethyl acetate and propyl acetate.

The concentration of the substrate in the organic solvent advantageously varies between 0.01 and 1 mol/l.

A basic compound can optionally be added after the formation of the hydrogenation complex.

This basic compound can be an alkali metal base such as sodium or potassium hydroxide, or a primary, secondary or tertiary amine and more particularly pyridine, piperidine or triethylamine, preferably triethylamine.

The amount of base added is such that the ratio of the number of mol of base to the number of metal atoms present in the diphosphine/transition metal complex is between 0 and 25, preferably between 0 and 12.

In the case where a simple ketone is used, it may be desirable to increase its reactivity by adding a chiral amine, preferably a primary diamine, and a base such as those mentioned above, more particularly potassium hydroxide. More specific examples of diamines which may be mentioned are 1,1-diphenyl-1,2-diaminoethane, 1,1-bis(4-methoxyphenyl)-2-methyl-1,2-diaminoethane, 1,1-bis(4-methoxyphenyl)-2-isopropyl-1,2-diaminoethane and 1,1-bis(4-methoxyphenyl)-2-isobutyl-1,2-diaminoethane.

Reference may be made to the article by Ryoji Noyori et al. [J. Am. Chem. Soc. 117, p. 2675 (1995)].

The amount of base generally represents 0.5 mol % of the substrate and the amount of diamine generally represents from 0.2 to 0.5 mol %.

A preferred embodiment of the process of the invention is given below.

Said process is carried but in an autoclave, which is purged with an inert gas, preferably nitrogen. It is preferable to introduce the substrate in solution in the organic solvent, followed by the catalyst, also in solution in the organic solvent.

The nitrogen is replaced by hydrogen.

The hydrogenation has ended when the hydrogen pressure becomes stable.

The hydrogenation process according to the invention provides access to the different enantiomers of numerous derivatives. Thus, depending on the substrate, different products are obtained, such as alcohols from the compounds of formula (Va) and hydroxylamines, amines, hydrazines or semicarbazines from the compounds of formulae $(Vb_1)$, $(Vb_2)$, $(Vb_3)$ and $(Vb_4)$ respectively.

The following Examples, which are given without implying a limitation, illustrate the present invention.

EXAMPLES

The ligand used in the metal complexes is prepared by the following procedure:

Phospholyllithium 11.3 g (0.06 mol) of 1-phenyl-3,4-dimethylphosphole, 0.8 g of lithium metal and 100 ml of distilled tetrahydrofuran are introduced into a 250 ml round-bottomed flask.

The mixture is stirred under argon for 2 hours in a cold water bath.

The solution turns brown.

The appearance of the phospholyllithium is monitored by $^{31}$P NMR.

$^{31}$P NMR: δ(THF)=55.8 ppm.

2.7 g of aluminium chloride are added at 0° C. to trap the phenyllithium.

The reaction is allowed to continue for 30 minutes at 0° C.

1,1'-Bisphosphole 6 g (0.025 mol) of diiodine in solution in 25 ml of tetrahydrofuran are added dropwise to the above mixture at room temperature.

When 90% of this solution has been introduced, the disappearance of the phospholyllithium is checked by $^{31}$P NMR.

$^{31}$P NMR: δ(THF)=−22.4 ppm.

The 1,1'-bisphosphole is extracted from the medium under nitrogen using hexane.

Bis[1-phospha-2,3-diphenyl-4,5-dimethylnorbornadiene]: (I m) and (I r)

The above solution is evaporated to dryness in the absence of air and heated to 140° C.

8 g of diphenylacetylene are then introduced and the reaction is allowed to continue for 15 to 20 minutes.

The disappearance of the 1,1'-bisphosphole is again followed by $^{31}$P NMR.

The spectrum is composed of 2 singlets corresponding to the two diastereoisomers.

The product is extracted with ether and washed with water.

The organic phases are combined and then evaporated to dryness.

The residue is then purified by chromatography on a silica column (elution with hexane to remove the excess diphenylacetylene and then with a hexane/dichloromethane mixture: 80/20 by volume).

The overall yield is 30%.

Palladium(II) complexes with (I m) and (I r), called (VI m) and (VI r)

5 g (8.25 mmol) of (I m) and (I r) are introduced into a 500 ml round-bottomed flask and dissolved in 200 ml of dichloromethane.

3 g (8.25 mmol) of $PdCl_2(PhCN)_2$ in 100 ml of dichloromethane are then added dropwise.

The reaction, which is carried out under argon, is immediate.

The solution is evaporated to dryness and the residue is chromatographed on silica to separate the two diastereoisomers.

Elution is performed with dichloromethane to remove the impurities, then with a dichloromethane/ethyl acetate mixture: 95/5 by volume to separate the racemate, and finally with a dichloromethane/ethyl acetate mixture: 80/20 by volume to separate the meso product.

$^{31}P$ NMR: $\delta(CH_2Cl_2)$=81.9 ppm—minority isomer corresponding to the racemate.

$^{31}P$ NMR: $\delta(CH_2Cl_2)$=88.1 ppm—majority isomer corresponding to the meso product.

Decomplexation of (VI r)

1.5 g (0.002 mol) of racemic (VI r) and 20 ml of dichloromethane are introduced into a 100 ml round-bottomed flask.

0.5 g of sodium cyanide and a few milliliters of water (3 ml) are then added.

The mixture is stirred vigorously under argon for 10 to 15 minutes.

The bis[1-phospha-2,3-diphenyl-4,5-dimethylnorbornadiene] (I r) is then extracted with dichloromethane.

The organic phase is washed with water and then dried over sodium sulfate.

Pure (I r) is thus recovered.

The overall yield of the separation of the diastereoisomers is 90%.

The racemic mixture (I r) is characterized as follows:

$^{31}P$ NMR: $\delta(CDCl_3)$=−13.2 ppm.

$^1H$ NMR: $\delta(CDCl_3)$=1.31 (s, 6H, $CH_3$); 1.69 (s, 6H, $CH_3$); 2.02–2.20 (m, 4H, $CH_2$ bridge); 6.86–7.29 (m, 20H, phenyls).

Binuclear palladium(II) complex 290 mg (0.5 mmol) of racemic (I r) and 300 mg (0.5 mmol) of (+)-di-$\mu$-chlorobis[(S)-N,N-dimethyl-α-phenylethylamine-2C,N]dipalladium(II) are introduced into 12 ml of benzene under nitrogen.

The complexation is rapid and is followed by $^{31}P$ NMR.

The brown solution is evaporated to dryness and the residue is chromatographed to separate the two diastereoisomers (elution with toluene/ethyl acetate: 80/20 by volume).

The two enantiomers are thus recovered; they are isolated pure in the form of two diastereoisomeric complexes of the formulae

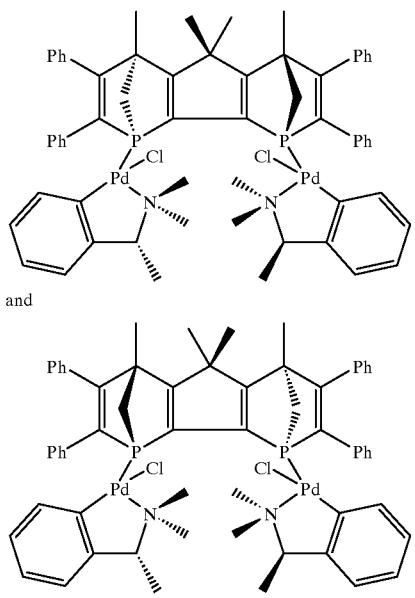

and

These enantiomers are recovered pure by decomplexing as for (VI r).

The diphosphines of formulae (Ia) and (Ib) are respectively identified as follows:

$^{31}P$ NMR: $\delta(CDCl_3)$=−13.2 ppm−$[\alpha]_D$=+231° (c=1, $C_6D_6$)

$^{31}P$ NMR: $\delta(CDCl_3)$=−13.2 ppm−$[\alpha]_D$=−198° (c=1, $C_6D_6$) ($[\alpha]_D$ being determined for a concentration of 10 mg/ml and at room temperature).

The diphosphines are used as ligands in the following Examples:

Example 1

This Example describes the preparation of a complex of the formula $[RuBr_2(P*P)]$.

7.5 mg of the phosphine of formula (Ia) (0.013 mmol) and 4 mg of the commercially available complex [Ru(COD)(meallyl)$_2$] (0.013 mmol) are dissolved in 2 ml of acetone in a 10 ml Schlenk tube under argon and at room temperature.

0.11 ml of a 0.29 M solution of hydrobromic acid in methanol (0.026 mmol) is then added dropwise.

The mixture is agitated for 30 min. The initially colourless solution turns brown.

The compound obtained after evaporation of the solvent is used without purification.

$^{31}P$ NMR (acetone): $\delta_A$=97.0 ppm $\delta_B$=87.0 ppm $^3J_{AB}$=21.0 Hz

Example 2

In this Example, the following compound:

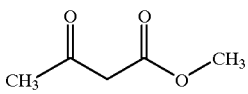

is subjected to asymmetric hydrogenation with the aid of the catalyst of Example 1.

0.1 ml of said compound is dissolved in 3 ml of methanol in a Schlenk tube.

The complex of Example 1 is then prepared as proposed above.

The acetone is evaporated off and the residue is dissolved in 2 ml of methanol.

The two solutions are then introduced into an autoclave which has first been purged and kept under a nitrogen atmosphere.

Hydrogen is then introduced up to a pressure of 4 atmospheres.

The mixture is agitated at 20° C. for 48 hours.

The excess hydrogen is evacuated and the reaction solution is recovered.

The solvent is evaporated off and the residue is analyzed by $^1$H NMR to check the progress of the reaction.

Methyl 3-hydroxybutanoate is obtained. The reaction is quantitative.

The enantiomeric excess is determined by chiral gas chromatography.

With the diphosphine (Ia), ee=80%.

Example 3

This Example describes the preparation of a complex of the formula $RuBr_2(P*P)$ in which (P*P) represents the diphosphine of formula (Ib).

Said complex is prepared by the procedure of Example 1.

Example 4

In this Example, the following compound:

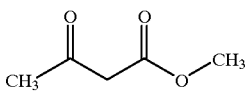

is subjected to asymmetric hydrogenation with the aid of the catalyst of Example 3.

The procedure is the same as in Example 2.

With the diphosphine (Ib), ee=81%.

Example 5

In this Example, the following compound:

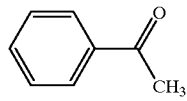

is subjected to asymmetric hydrogenation with the aid of the catalyst of Example 1.

780 mg (6.5 mmol) of ketone are dissolved in 7 ml of isopropanol in a 10 ml Schlenk tube under argon.

2.75 mg of the commercially available chiral diamine (S,S)-1,2-diphenyl-1,2-ethanediamine and 1.45 mg of potassium hydroxide are added.

This solution is agitated thoroughly until the mixture is homogeneous.

Likewise, the catalyst of Example 1 is dissolved in 2 ml of isopropanol.

The two solutions are introduced into the autoclave with the aid of a syringe.

Hydrogen is added up to a pressure of 5 atm.

The mixture is agitated for 15 h at 25° C.

The excess hydrogen is evacuated and the reaction solution is recovered.

After evaporation of the solvent, the progress of the reaction is monitored by $^1$H NMR of the crude product.

Degree of conversion=45%.

The alcohol is then purified by vacuum distillation in a bulb tube apparatus (Kugelrohr®).

The configuration of the alcohol is determined by the sign of the optical rotation $[\alpha]_D > 0$ (c=1, ether).

The enantiomeric excess is determined by chiral HPLC on a Daicel Chiracel OD column (n-hexane/ethanol-95/5; 0.5 ml/min):

$t_R$ (S)-1-phenylethanol=14.6 min; ($t_R$=retention time)
$t_R$ (R)-1-phenylethanol=17.0 min;
ee=57% (R).

Example 6

In this Example, the following compound:

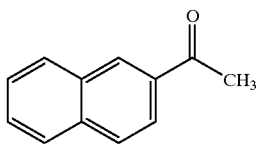

is subjected to asymmetric hydrogenation with the aid of the catalyst of Example 1.

1.098 g of said compound are dissolved in 7 ml of isopropanol in a Schlenk tube.

The subsequent procedure is as in Example 5.

Hydrogenation is carried out for 10 h.

The yield calculated by $^1$H NMR is 60%.

The enantiomeric excess is determined by $^1$H NMR of the ester formed with the commercially available (R)-(+)-α-methoxytrifluoromethylphenylacetic acid (MTPA).

In the absence of air, 70 mg of MTPA, 0.3 ml of a commercially available 1 M solution of 1,3-dicyclohexylcarbodiimide (DCC) in dichloromethane and 50 mg of p-dimethylaminopyridine are added to 50 mg of the alcohol dissolved in 4 ml of dichloromethane.

This mixture is agitated overnight at room temperature.

After evaporation of the solvent, the ester is extracted with ether.

ee=81% (R).

Example 7

This Example describes the preparation of a complex of the formula $[Ir(COD)(P*P)]^+X^-$, in which COD is 1,5- cyclooctadiene, P*P represents the diphosphine Ib and X⁻ is the anion BPh$_4^-$.

4.35 mg of the commercially available precursor [Ir(COD)Cl]$_2$ are dissolved in 1 ml of a benzene/MeOH mixture (1:1 by volume) in a 10 ml Schlenk tube under argon. A solution of 7.5 mg of the diphosphine Ib in 1 ml of the same solvent mixture is then added dropwise.

After agitation for 15 min, the expected complex is obtained.

The solvent is evaporated off.

The red powder obtained is washed twice with isopropanol and redissolved in 1 ml of dichloromethane.

1.5 equivalents of commercially available NaBPh$_4$ (7.2 mg) are then added.

The solution is concentrated on a vacuum pump (0.2 mm of mercury) and the complex precipitates.

$^{31}$P NMR: $\delta(CD_2Cl_2)$=64.5 ppm.

Example 8

In this Example, the following compound:

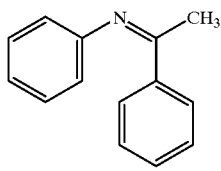

is subjected to asymmetric hydrogenation with the aid of the catalyst of Example 7.

506 mg of said compound are dissolved in 3 ml of a toluene/methanol mixture (1:1 by volume) in a Schlenk tube under argon.

A solution of 3 ml of the catalyst of Example 7 in the same solvent mixture is prepared in a second Schlenk tube. The commercially available cocatalyst Bu$_4$N$^+$I$^-$ (10 mg) is then added.

The two solutions are then introduced consecutively with the aid of a syringe into an autoclave which has first been purged and kept under a nitrogen atmosphere.

Hydrogen is then introduced twice up to a pressure of 3 atm. in order to purge the autoclave.

The pressure is finally increased to 20 atm.

The mixture is agitated for 48 h at 25° C.

After evaporation of the solvent, the 50% progress of the reaction is monitored by $^1$H NMR of the crude product.

The latter is purified by distillation and the enantiomeric excess is evaluated by measurement of the optical rotation: ee=20% (S).

What is claimed is:

1. Process for the asymmetric hydrogenation of a ketonic compound or a derivative thereof, wherein the asymmetric hydrogenation of said compound or a derivative thereof is carried out in the presence of an effective amount of a metal complex comprising, as the ligand, an optically active diphosphine having one of the following formulae:

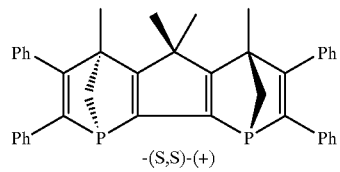

(Ia)

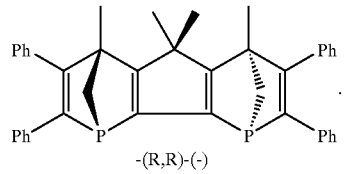

(Ib)

2. Process according to claim 1, wherein the metal complex comprises an optically active diphosphine of formula (Ia) or (Ib) and a transition metal selected from the group consisting of rhodium, ruthenium, rhenium, iridium, cobalt, nickel, platinum and palladium.

3. Process according to claim 1, wherein the metal complex has one of the following formulae:

[RuY$_1$Y$_2$(P*P)]     (IVa)

[RuY$_1$Y$_2$(P*P)]     (IVb)

in which:
(P*P) in formula (IVa) is the diphosphine of formula (Ia) and in formula (IVb) is the diphosphine of formula (Ib); and Y$_1$ and Y$_2$, which are identical or different, are each independently selected from PF$_6^-$, PCl$_6^-$, BF$_4^-$, BCl$_4^-$, SbF$_6^-$, SbCl$_6^-$, BPh$_4^-$, ClO$_4^-$ and CF$_3$SO$_3^-$; a halogen atom; and a carboxylate anion.

4. Process according to claim 1, wherein the metal complex has one of the following formulae:

[RuY$_1$Ar(P*P)Y$_2$]     (IVc)

[RuY$_1$Ar(P*P)Y$_2$]     (IVd)

in which:
(P*P) in formula (IVc) is the diphosphine of formula (Ia) and in formula (IVd) is the diphosphine of formula (Ib);

Ar is benzene, p-methylisopropylbenzene or hexamethylbenzene;

Y$_1$ is a halogen atom; and

Y$_2$ is PF$_6^-$, PCl$_6^-$, BF$_4^-$, BCl$_4^-$, SbF$_6^-$, SbCl$_6^-$, BPh$_4^-$, ClO$_4^-$ or CF$_3$SO$_3^-$.

5. Process according to claim 1, wherein the ketonic compound or a derivative thereof is of formula (V):

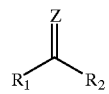

(V)

in which:
R$_1$ is different from R$_2$;
R$_1$ and R$_2$ are independently selected from a substituted or unsubstituted hydrocarbon radical having from 1 to 30 carbon atoms; or R₁ and R₂ can form a ring optionally comprising a heteroatom; and Z is oxygen or —NH or a functional group comprising at least one of oxygen or nitrogen.

6. Process according to claim 5, wherein the ketonic compound or a derivative thereof is of formula (V) in which the radicals R₁ and R₂ are a substituted or unsubstituted, monovalent hydrocarbon radical which can be a linear or branched, saturated or unsaturated, acyclic aliphatic radical or a monocyclic or polycyclic, saturated, unsaturated or aromatic carbocyclic or heterocyclic radical.

7. Process according to claim 5, wherein the ketonic compound or a derivative thereof has formula (Va):

(Va)

in which:
R₁ is different from R₂, the radicals R₁ and R₂ being a hydrocarbon radical having from 1 to 30 carbon atoms and optionally comprising one or more of a ketone, an acid, ester, thioacid or thioester; or
R₁ and R₂ can form a substituted or unsubstituted carbocyclic or heterocyclic ring having 5 or 6 atoms.

8. Process according to claim 7, wherein the ketonic compound is a ketone wherein R₁ and R₂ are independently selected from a linear alkyl radical of 1–4 carbons and a branched alkyl radical of 1–4 carbons.

9. Process according to claim 1, wherein the ketonic compound has formula (Va₁):

(Va₁)

in which:
R₁ and R₂ are independently selected from:
a linear or branched alkyl radical having from 1 to 12 carbon atoms;
an alkenyl radical having from 2 to 12 carbon atoms;
an optionally substituted phenyl, naphthyl or benzyl radical;
a triphenylmethyl radical; and
a radical of the formula
—R₃—OH
—R₃—O—R₄
—R₃—CO—R₄
—R₃—COOR₄
—R₃—CHO
—R₃—NO₂
—R₃—CN
—R₃—N(R₄)₂
—R₃—CO—N(R₄)₂
—R₃—PO—(OR₄)₂
—R₃—SH
—R₃—X or
—R₃—CF₃
in which R₃ is a valence bond or a saturated or unsaturated, linear or branched, divalent hydrocarbon radical having from 1 to 6 carbon atoms; the radicals R₄, which are identical or different, are selected from a hydrogen atom, a linear or branched alkyl radical having from 1 to 6 carbon atoms, a benzyl radical and a phenyl radical; and X symbolizes a halogen atom; or
R₁ and R₂ can form a substituted or unsubstituted carbocyclic or heterocyclic ring having 5 or 6 atoms.

10. Process according to claim 9, wherein the ketonic compound of formula (Va₁) is selected from:

methyl phenyl ketone,
isopropyl phenyl ketone,
cyclopropyl phenyl ketone,
allyl phenyl ketone,
p-methylphenyl methyl ketone,
benzyl phenyl ketone,
phenyl triphenylmethyl ketone,
o-bromoacetophenone,
α-bromoacetone,
α-dibromoacetone,
α-chloroacetone,
α-dichloroacetone,
α-trichloroacetone,
1-chloro-3,3-dichloroacetone,
1-chloro-2-oxobutane,
1-fluoro-2-oxobutane,
1-chloro-3-methyl-2-butanone,
α-chloroacetophenone,
1-chloro-3-phenylacetone,
α-methylaminoacetone,
α-dimethylaminoacetone,
1-butylamino-2-oxopropane,
1-dibutylamino-2-oxopropane,
1-methylamino-2-oxobutane,
1-dimethylamino-2-oxobutane,
1-dimethylamino-3-methyl-2-oxobutane,
1-dimethylamino-2-oxopentane,
α-dimethylaminoacetophenone,
α-hydroxyacetone,
1-hydroxy-3-methyl-2-butanone,
1-hydroxy-2-oxobutane,
1-hydroxy-2-oxopentane,
1-hydroxy-2-oxohexane,
1-hydroxy-2-oxo-3-methylbutane,
α-hydroxyacetophenone,
1-hydroxy-3-phenylacetone,
α-methoxyacetone,
α-methoxyacetophenone,
α-ethoxyacetone,
α-butoxyacetophenone,
α-chloro-p-methoxyacetophenone,
α-naphthenone,
1-ethoxy-2-oxobutane,
1-butoxy-2-oxobutane,
α-dimethoxyphosphorylacetone, and
3-oxotetrahydrothiophene.

11. Process according to claim 7, wherein the ketonic compound is a diketone.

12. Process according to claim 7, wherein the ketonic compound has formula (Va₂):

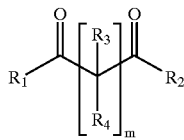

in which:
   m is equal to 0, 1, 2 or 3;
   the radicals $R_1$ and $R_2$, which are different, are selected from:
      a linear or branched alkyl radical having from 1 to 12 carbon atoms;
      an alkenyl radical having from 2 to 12 carbon atoms;
      an optionally substituted phenyl, naphthyl or benzyl radical; and
      a radical of the formula
         —$R_5$—OH
         —$R_5$—O—$R_6$
         —$R_5$—CO—$R_6$
         —$R_5$—COO$R_6$
         —$R_5$—N($R_6$)$_2$
         —$R_5$—CO—N($R_6$)$_2$
         —$R_5$—PO—(O$R_6$)$_2$
         —$R_5$—SH
   —$R_5$—X or
   —$R_5$—CF$_3$
      in which $R_5$ is a valence bond or a saturated or unsaturated, linear or branched, divalent hydrocarbon radical having from 1 to 6 carbon atoms; the radicals $R_6$, which are identical or different, are selected from a hydrogen atom, a linear or branched alkyl radical having from 1 to 6 carbon atoms, a benzyl radical and a phenyl radical; and X symbolizes a halogen atom; or
   one of the radicals $R_1$ or $R_2$ is a hydrogen atom; and the radicals $R_3$ and $R_4$, which are identical or different, are selected from:
   a hydrogen atom;
   a linear or branched alkyl radical having from 1 to 12 carbon atoms;
   a halogen atom; and
   —$R_5$—COO$R_6$, in which $R_5$ and $R_6$ are as defined above; or
   $R_1$ or $R_2$ and $R_3$ or $R_4$ can form a substituted or unsubstituted carbocyclic or heterocyclic ring having 5 or 6 atoms.

13. Process according to claim 12, wherein the ketonic compound of formula (Va$_2$) is selected from:

α-formylacetone,
diacetyl,
3,4-dioxohexane,
4,5-dioxooctane,
1-phenyl-1,2-dioxopropane,
1-phenyl-2,3-dioxobutane,
dibenzoyl,
p-methoxydibenzoyl,
1,2-cyclopentanedione,
1,2-cyclohexanedione,
acetylacetone,
3,5-heptanedione,
4,6-nonanedione,
5,7-undecanedione,
2,4-hexanedione,
2,4-heptanedione,
2,4-octanedione,
2,4-nonanedione,
3,5-nonanedione,
3,5-decanedione,
2,4-dodecanedione,
1-phenyl-1,3-butanedione,
1-phenyl-1,3-pentanedione,
1-phenyl-1,3-hexanedione,
1-phenyl-1,3-heptanedione,
3-methyl-2,4-pentanedione,
1,3-diphenyl-1,3-propanedione,
1,5-diphenyl-2,4-pentanedione,
1,3-di(trifluoromethyl)-1,3-propanedione,
3-chloro-2,4-pentanedione,
1,5-dichloro-2,4-pentanedione,
1,5-dihydroxy-2,4-pentanedione,
1,5-dibenzyloxy-2,4-pentanedione,
1,5-diamino-2,4-pentanedione,
1,5-di(methylamino)-2,4-pentanedione,
1,5-di(dimethylamino)-2,4-pentanedione,
methyl 3,5-dioxohexanoate,
3-carbomethoxy-2,4-pentanedione,
3-carboethoxy-2,4-pentanedione,
1,3-cyclopentanedione,
1,3-cyclohexanedione,
1,3-cycloheptanedione,
5-carboethoxy-1,3-cyclopentanedione,
2-acetyl-1-cyclopentanone, and
2-acetyl-1-cyclohexanone.

14. Process according to claim 7, wherein the ketonic compound is a keto acid, keto thioacid or a derivative thereof.

15. Process according to claim 7, wherein the ketonic compound has formula (Va$_3$) or (Va$_4$):

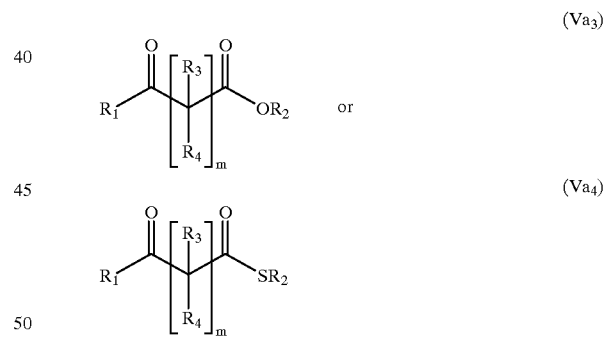

in which:
   m is equal to, 0, 1, 2 or 3;
   the radical $R_1$ is selected from:
      a linear or branched alkyl radical having from 1 to 12 carbon atoms;
      an alkenyl radical having from 2 to 12 carbon atoms;
      an optionally substituted phenyl, naphthyl or benzyl radical; and
      a radical of the formula
         —$R_5$—OH
         —$R_5$—O—$R_6$
         —$R_5$—CO—$R_6$
         —$R_5$—COO$R_6$
         —$R_5$—N($R_6$)$_2$
         —$R_5$—CO—N($R_6$)$_2$ —$R_5$—PO—$(OR_6)_2$
—$R_5$—SH
—$R_5$—X or
—$R_5$—$CF_3$ in which $R_5$ is a valence bond or a saturated or unsaturated, linear or branched, divalent hydrocarbon radical having from 1 to 6 carbon atoms; the radicals $R_6$, which are identical or different, are selected from a hydrogen atom, a linear or branched alkyl radical having from 1 to 6 carbon atoms, a benzyl radical and a phenyl radical; and X symbolizes a halogen atom;

the radical $R_2$ is selected from:
a hydrogen atom;
a linear or branched alkyl radical having from 1 to 6 carbon atoms;
a benzyl radical; and
a phenyl radical; and the radicals $R_3$, and $R_4$, which are identical or different, are selected from:
a hydrogen atom;
a linear or branched alkyl radical having from 1 to 12 carbon atoms;
a halogen atom;
—$R_5$—$COOR_6$, in which $R_5$ and $R_6$ are as defined above; and
—$R_5$—CO—$N(R_6)_2$, in which $R_5$ and $R_6$ are as defined above; or $R_1$ and $R_2$ or $R_1$ and $R_3$ or $R_1$ and $R_4$ or $R_2$ and $R_4$ form a substituted or unsubstituted carbocyclic or heterocyclic ring having 5 or 6 atoms.

16. Process according to claim 15, wherein the ketonic compound of formula ($Va_3$) or ($Va_4$) is selected from:

2-acetylbenzoic acid,
pyruvic acid,
2-oxobutanoic acid,
3-methyl-2oxobutanoic acid,
phenylglyoxylic acid,
phenylpyruvic acid,
p-methoxyphenylpyruvic acid,
3,4-dimethoxyphenylpyruvic acid,
methyl acetoacetate,
ethyl acetoacetate,
n-propyl acetoacetate,
isopropyl acetoacetate,
n-butyl acetoacetate,
t-butyl acetoacetate,
n-pentyl acetoacetate,
n-hexyl acetoacetate,
n-heptyl acetoacetate,
n-octyl-acetoacetate,
methyl 3-oxopentanoate,
methyl 3-oxohexanoate,
methyl 3-oxoheptanoate,
ethyl 3-oxooctanoate,
ethyl 3-oxononanoate,
ethyl 3-oxodecanoate,
ethyl 3-oxoundecanoate,
ethyl 3-oxo-3-phenylpropionate,
ethyl 4-phenyl-3-oxobutanoate,
methyl 5-phenyl-3-oxopentanoate,
ethyl 3-oxo-3-p-methoxyphenylpropionate,
methyl 4-chloroacetoacetate,
ethyl 4-chloroacetoacetate,
methyl 4-fluoroacetoacetate,
ethyl 3-trifluoromethyl-3-oxopropionate,
ethyl 4-hydroxy-3-oxobutanoate,
methyl 4-methoxyacetoacetate,
methyl 4-tert-butoxyacetoacetate,
methyl 4-benzyloxy-3-oxobutanoate,
ethyl 4-benzyloxy-3-oxobutanoate,
methyl 4-amino-3-oxobutanoate,
ethyl 3-methylamino-3-oxobutanoate,
methyl 4-dimethylamino-3-oxobutanoate,
ethyl 4-dimethylamino-3-oxobutanoate,
methyl 2-methylacetoacetate,
ethyl 2-methylacetoacetate,
ethyl 2-chloroacetoacetate,
diethyl 2-acetylsuccinate,
diethyl 2-acetylglutarate,
dimethyl acetylmalonate,
thiomethyl acetoacetate,
thioethyl acetoacetate,
thiophenyl acetoacetate,
methyl pyruvate,
ethyl 3-methyl-2-oxobutanoate,
ethyl phenylglyoxylate,
methyl phenylpyruvate,
ethyl phenylpyruvate,
3-oxobutanoic dimethylamide,
3-oxobutanoic benzylamide,
2-carboethoxycyclopentanone,
2-carboethoxycyclohexanone,
ketopentalactone,
4-oxopentanoic acid,
4-oxohexanoic acid,
4-oxoheptanoic acid,
4-oxodecanoic acid,
4-oxododecanoic acid,
4-phenyt-4-oxybutyric acid,
4p-methoxyphenyl-4-oxybutyric acid,
4-(3,4-dimethoxyphenyl)-4-oxobutyric acid,
4-(3,4 5-trimethoxyphenyl)-4-oxobutyric acid,
4-p-chlorophenyl-4-oxybutyric acid, and
4-phenyl-4-oxobutyric acid.

17. Process according to claim 7, wherein the ketonic compound has formula (Va) in which the radicals $R_1$ and $R_2$ form, with the carbon atom carrying the carbonyl group, one or more saturated, unsaturated or aromatic rings comprising 5 or 6 carbon atoms in each ring.

18. Process according to claim 5, wherein the ketonic derivative has formula (Vb):

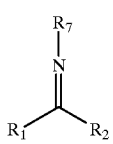

(Vb)

in which:

$R_1$ and $R_2$, which are different, are as defined in claim 5; and $R_7$ is:
a hydrogen atom;
a hydroxyl group;
a group $OR_8$;
a hydrocarbon radical $R_8$;

a group of the formula

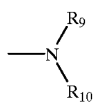

or a group of the formula

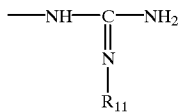

where $R_8$, $R_9$, $R_{10}$ and $R_{11}$ are selected from a hydrogen atom and a hydrocarbon group having from 1 to 30 carbon atoms.

19. Process according to claim 18, wherein the ketonic derivative has one of the following formulae:

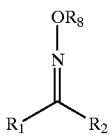 (Vb$_1$)

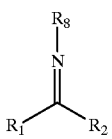 (Vb$_2$)

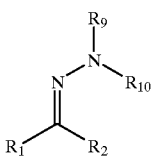 (Vb$_3$)

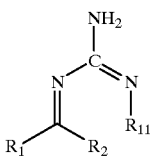 (Vb$_4$)

in which:
the radicals $R_1$, $R_2$ and $R_8$ to $R_{11}$ are selected from:
a linear or branched alkyl radical having from 1 to 12 carbon atoms;
a cycloalkyl radical having from 5 to 12 carbon atoms;
an aryl radical having from 6 to 12 carbon atoms;
an aralkyl radical having from 7 to 12 carbon atoms;
an aryl radical having from 6 to 12 carbon atoms carrying substituents selected from an alkyl or alkoxy radical having from 1 to 4 carbon atoms; an amino, $(C_1-C_4)$-alkylamino or di$(C_1-C_4)$alkylamino; a nitro; a halogen atom and a $(C_1-C_4)$ alkoxycarbonyl group;
a saturated or unsaturated heterocyclic radical;
an alkanoyl radical having from 1 to 12 carbon atoms;
an arylcarbonyl radical having from 6 to 12 carbon atoms; and
an arylalkanoyl radical having from 6 to 12 carbon atoms; or $R_1$ and $R_2$, $R_1$ and $R_8$, $R_2$ and $R_8$, $R_1$ and $R_9$, $R_2$ and $R_{10}$, $R_1$ and $R_{12}$, or $R_2$ and $R_{11}$ can form a substituted or unsubstituted, monocyclic or polycyclic carbocyclic or heterocyclic ring having 5 or 6 atoms in each ring.

20. Process according to claim 18, wherein the ketonic derivative has one of formulae (Vb$_1$) to (Vb$_4$) in which the radicals $R_1$, $R_2$ and $R_8$ to $R_{11}$, which are identical or different, are selected from:

a linear or branched alkyl radical having from 1 to 4 carbon atoms;

a cyclopentyl or cyclohexyl radical;

a phenyl radical;

a benzyl or phenylethyl radical;

a phenyl radical having one or more substituents selected from an alkyl or alkoxy radical having from 1 to 4 carbon atoms; an amino, $(C_1-C_4)$alkylamino or di$(C_1-C_4)$alkylamino; a nitro; a halogen atom and a $(C_1-C_4)$alkoxycarbonyl group;

a naphthyl radical;

a saturated or unsaturated, oxygen-containing or nitrogen-containing heterocyclic radical having 5 or 6 atoms;

an acetyl radical or a benzoyl radical; and an arylalkanoyl radical having from 6 to 12 carbon atoms.

21. Process according to claim 18, wherein the ketonic derivative is selected from:

acetophenone oxime,
N-isobutyl-2-iminopropane,
N-isobutyl-1-methoxy-2-iminopropane,
N-benzyl-1-imino-1-(phenyl)ethane,
N-benzyl-1-imino-1-(4-methoxyphenyl)ethane,
N-benzyl-1-imino-1-(2-methoxyphenyl)ethane,
N-phenyl-2-iminopentane,
N-(2,6-dimethylphenyl)-2-iminopentane,
N-(2,4,6-trimethylphenyl)-2-iminopentane,
N-phenyl-1-imino-1-phenylethane,
N-phenyl-1-methoxy-2-iminopropane,
N-(2,6-dimethylphenyl)-1-methoxy-2-iminopropane,
N-(2-methyl-6-ethylphenyl)-1-methoxy-2-iminopropane,
1-cyclohexyl-1-(2-benzoylhydrazono)ethane,
1-phenyl-1-(2-benzoylhydrazono)ethane,
1-p-methoxyphenyl-1-(2-benzoylhydrazono)ethane,
1-p-ethoxyphenyl-1-(2-benzoylhydrazono)ethane,
1-p-nitrophenyl-1-(2-benzoylhydrazono)ethane,
1-p-bromophenyl-1-(2-benzoylhydrazono)ethane,
1-p-carboethoxyphenyl-1-(2-benzoylhydrazono)ethane,
1,2-diphenyl-1-(2-benzoylhydrazono)ethane,
3-methyl-2-(2-p-dimethylaminobenzoylhydrazono)butane,
1-phenyl-1-(2-p-methoxybenzoylhydrazono)ethane,
1-phenyl-1-(2-p-dimethylaminobenzoylhydrazono)ethane,
ethyl 2-(2-benzoylhydrazono)propionate,
methyl-2-(2-benzoylhydrazono)butyrate,
methyl 2-(2-benzoylhydrazono)valerate,
methyl 2-phenyl-2-(2-benzoylhydrazono)acetate, and the following cyclic ketoimines with an endocyclic or exocyclic bond:

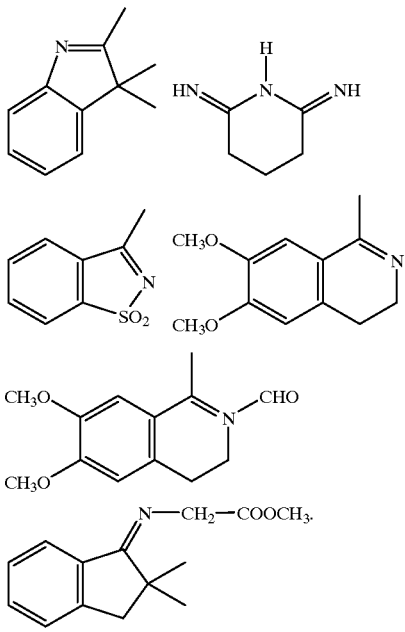

22. Process according to claim 1, wherein the hydrogenation is carried out at a temperature between 20 and 100° C.

23. Process according to claim 1, wherein the hydrogen pressure is between 0.1 and 200 bar.

24. Process according to claim 1, wherein at least one metal complex is used, said metal complex comprising an optically active diphosphine of formula (Ia) or (Ib) and a transition metal selected from the group consisting of rhodium, ruthenium, rhenium, iridium, cobalt, nickel, platinum and palladium.

25. Process according to claim 1, wherein the ratio of the number of metal atoms present in the complex to the number of mol of compound to be hydrogenated is between 0.1 and 0.0001.

26. Process according to claim 1, wherein a basic compound is added after the formation of the hydrogenation compound.

27. Process according to claim 1 wherein a primary diamine is added.

28. Process according to claim 1, wherein the metal complex has one of the following formulae:

[ML$_2$(P*P)]Y (IIa)

[ML$_2$(P*P)]Y (IIb)

in which:

(P*P) in formula (IIa) is the diphosphine of formula (Ia) and in formula (IIb) is the diphosphine of formula (Ib);

M is rhodium or iridium;

Y is an anion selected from $PF_6^-$, $PCl_6^-$, $BF_4^-$, $BCl_4^-$, $SbF_6^-$, $SbCl_6^-$, $BPh_4^-$, $ClO_4^-$, $CN^-$ and $CF_3SO_3^-$; a halogen; a 1,3-diketonate; alkylcarboxylate or halogenoalkylcarboxylate anion with a lower alkyl radical; or a phenylcarboxylate or phenate anion whose benzene ring is optionally substituted by lower alkyl radicals and/or halogen atoms; and L is an olefin having from 2 to 12 carbon atoms and two ligands L can be bonded together to form a polyunsaturated, linear or cyclic hydrocarbon chain.

29. Process according to claim 1, wherein the metal complex has one of the following formulae:

[IrL(P*P)]Y (IIIa)

[IrL(P*P)]Y (IIIb)

in which (P*P) in formula (IIIa) is the diphosphine of formula (Ia) and in the formula (IIIb) is the diphosphine of formula (Ib), L is an olefin having from 2 to 12 carbon atoms and two ligands L can be bonded together to form polyunsaturated, linear or cyclic hydrocarbon chain; and Y is an anion selected from $PF_6^-$, $PCl_6^-$, $BF_4^-$, $BCl_4^-$, $SbF_6^-$, $SbCl_6^-$, $BPh_4^-$, $ClO_4^-$, $CN^-$ or $CF_3SO_3^-$, a halogen; a 1,3-diketonate; alkylcarboxylate or halogenoalkylcarboxylate anion with a lower alkyl radical; or a phenylcarboxylate or phenate anion whose benzene ring is optionally substituted by lower alkyl radicals and/or halogen atoms.

* * * * *